United States Patent [19]

Prisbylla

[11] Patent Number: 4,714,491
[45] Date of Patent: Dec. 22, 1987

[54] DIPHENYL ETHER HERBICIDES

[75] Inventor: Michael P. Prisbylla, Richmond, Calif.

[73] Assignee: Stauffer Chemical Company, Westport, Conn.

[21] Appl. No.: 539,784

[22] Filed: Oct. 7, 1983

[51] Int. Cl.$^4$ .......................... A01N 57/02; C07F 9/40
[52] U.S. Cl. ......................................... 71/86; 558/193
[58] Field of Search ............................ 260/950; 71/86; 558/193

[56] References Cited

U.S. PATENT DOCUMENTS 4,322,375  3/1982  Maier et al. ..................... 260/951
4,419,123  12/1983  Swithenbank ..................... 71/86
4,434,108  2/1984  Maier ..................... 260/951

FOREIGN PATENT DOCUMENTS 154194  3/1981  Japan ..................... 260/951

OTHER PUBLICATIONS

Derwent, Abstract of Japanese 154,194.

Primary Examiner—Anton H. Sutto
Attorney, Agent, or Firm—Paul R. Martin

[57] ABSTRACT

As compounds, diphenyl ether derivatives of the formula

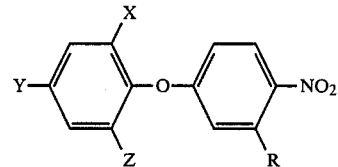

wherein X, Y and Z are the same or different and are selected from the group consisting of trifluoromethyl, halogen and hydrogen, and wherein R is selected from those having the formula

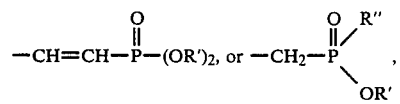

in which R' and R'' are selected from the group consisting of lower alkyl groups having from 1 to 3 carbon atoms, and agriculturally acceptable salts thereof.

10 Claims, No Drawings

DIPHENYL ETHER HERBICIDES

BACKGROUND OF THE INVENTION

The present invention relates to certain phosphorus-containing derivatives of diphenyl ether compounds which are particularly useful as pre- and post-emergent herbicides against annual and perennial grasses, as well as broadleaf weed pests.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

THE PRIOR ART

The prior art is full with examples of diphenyl ether compounds which have been disclosed to be herbicidally effective against grasses and broad leaf weed pests. Examples of such prior art references include U.S. Pat. No. 3,080,225, which discloses diphenyl ether compounds as being effective herbicides. Stil other prior art patents relating to diphenyl ethers include European Pat. Nos. 0,056,119 and 0,066,989 and Japanese Pat. No. 81-38641.

Efforts are constantly being made, however, to find compounds which are equal to or greater in effectiveness than presently existing compounds, or which are more economical to produce, or which have efficacy against classes of weed pests not shown by the prior art.

The present invention is directed to such compounds and methods of application.

DESCRIPTION OF THE INVENTION

It has now been discovered that certain new and novel phosphorus-containing derivatives of diphenyl ether compounds have good herbicidal and plant growth regulating activity, particularly when applied as post-emergent herbicides and used against broadleaf weed pests.

As used herein, the term "herbicide" means a compound or composition which controls or modifies the growth of plants. By the term "herbicidally effective amount" is meant any amount of such compound or composition which causes a modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing and the like.

The new and novel compounds of this invention are diphenyl ether compounds of the formula

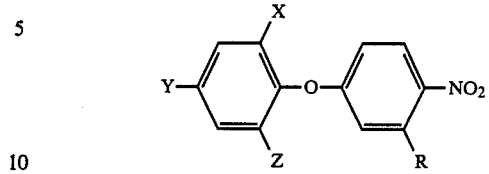

wherein X, Y and Z are the same or different and are selected from the group consisting of trifluoromethyl, halogen, and hydrogen, and wherein R is selected from those having the formula

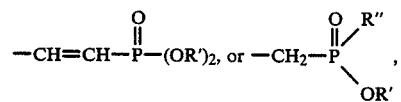

in which R' and R" are selected from the group consisting of lower alkyl groups having from 1 to 3 carbon atoms, and agriculturally acceptable salts thereof. The compounds are effective herbicide compounds in both pre-emergent and post-emergent applications and have been found to be particularly effective against broadleaf weeds when used in conjunction with or against the weeds growing in such crops as soybeans, rice, wheat, barley, etc.

Preferably, X is chlorine, Y is trifluoromethyl or chlorine and Z is hydrogen.

Examples of preferred compounds falling within the structural formula set forth above include: 2-nitro-5-[2-chloro-4-trifluoromethylphenoxy]styryl-3-O,O-dimethylphosphonate; 2-nitro-5-[2-chloro-4-trifluoromethylphenoxy]styryl-3'-phosphonic acid mono-isopropylamine salt; O-methyl, 2-nitro-5-[2-chloro-4-trifluoromethylphenoxy]benzylmethylphosphinate; 2-nitro-5-[2-chloro-4-trifluoromethylphenoxy]styryl-3'-O,O-diethylphosphonate; 2-nitro-5-[2,4-dichlorophenoxy]styryl-3'-O,O-diethylphosphonate; O-methyl-2-bromo-5-[2-chloro-4-trifluoromethylphenoxy]benzylmethylphosphinate; and O-ethyl-2-bromo-5-[2-chloro-4-trifluoromethylphenoxy]benzylmethyl phosphinate.

These compounds can be made by a couple of different ways involving the Wadsworth-Emmons reaction, as described in *Organic Reactions*, Vol. 25, p. 73 (John Wiley & Sons, 1977) or the Mihaelis-Arbuzov reaction as described in *Organic Reactions*, Vol. 6, p. 273 (John Wiley & Sons, 1951), as is illustrated in the examples below.

The following examples illustrate methods of making the compounds of the present invention.

EXAMPLE 1

Preparation of 2-Nitro-5-(2-chloro-4-trifluoromethylphenoxy)styryl-3 O,O-dimethyl phosphonate A round-bottom flask was obtained, and into this flask was charged 4.36 g (18.8 mM) of tetramethylenediphosphonate in 20 ml of tetrahydrofuran, and this was added dropwise to a suspension of 49.8 mM sodium hydride in 20 ml of tetrahydrofuran. The reaction was modulated with a water bath at ice temperature. After completion of the addition, the ice-bath was removed and the solution stirred for approximately 0.5 hour. The solution which had increased in temperature, was then recooled and 18.8 mM 5-[2-chloro-4-trifluoromethylphenoxy]-2-nitrobenzaldehyde dissolved in 20 ml of tetrahydrofuran was added dropwise. The ice-bath was removed after one hour an the solution allowed to stir for 3 hours. One hundred ml of water was then added and the solution extracted 3 times with ethyl acetate (200 ml total). The combined extracts were washed with a brine solution and dried over magnesium sulfate, filtered and concentrated to yield 8.1 g of the desired product, which was identified as such product by suitable analytical techniques.

EXAMPLE 2

Preparation of
2-Nitro-(2-chloro-4-trifluoromethylphenoxy)-strylyl-3'-phosphonic acid, mono-isopropylamine salt 1.4 g (3.3 mM) of 2-nitro-(2-chloro-4-trifluoromethylphenoxy)-styryl-3'-phosphonic acid was taken up into 20 ml of methyl chloride and treated with isopropyl amine (19.5 mM) and the solution was stirred for approximately 3 hours. The solution was then concentrated and identified by ir and nmr techniques as being the subject compound.

The foregoing examples are illustrative of general methods of preparing the compounds of the instant invention. Other compounds falling within the scope of the invention can be prepared in an analogous manner starting with the appropriate starting materials as outlined above.

The herbicidal activity of the compounds of the invention are exhibited by means of tests in accordance with the following procedure.

EXAMPLE 3

Herbicidal Activity Tests

This example offers herbicidal activity test data to show the effectiveness of the diphenyl ether compounds of the invention. The effect is observed by comparing the extent of weed control in test flats treated with the compounds against that occurring in similar control flats. The soil used in these tests was a sandy loam soil from the Livermore, Calif. area.

Also added to the soil was 17-17-17 fertilizer (N-$P_2O_5$-$K_2O$ on a weight basis), amounting to 50 ppm by weight with respect to the soil and 100 ppm Captan, a soil fungicide.

The treated soil was then placed in flats which were 3 inches deep, 6 inches wide, and 10 inches long. The soil was tamped and leveled with a row marker to impress six rows across the width of the flat. The test weeds were as follows:

| COMMON NAME | SCIENTIFIC NAME | ABR |
|---|---|---|
| Broadleaf Weeds: | | |
| A. annual morningglory | *Ipomoea purpurea* | AMG |
| B. cocklebur | *Xanthium sp.* | CB |
| C. hemp sesbania | *Sesbania exaltata* | SESB |
| D. velvetleaf | *Abutilon theophrasti* | VL |
| E. mustard | *Brassica sp.* | MD |
| F. nightshade | *Solanum sp.* | SP |
| G. pigweed | *Amaranthus sp.* | PW |
| Grasses: | | |
| H. yellow nutsedge | *Cyperus exculentus* | YNS |
| I. downybrome | *Bromus tectorum* | DB |
| J. foxtail | *Setaria sp.* | FT |
| K. annual ryegrass | *Lolium multiflorum* | ARG |
| L. watergrass | *Echinochloa crusgalli* | WG |
| M. rox-orange sorghum | *Sorghum bicolor* | SHC |
| N. wild oat | *Avena fatua* | WO |

Sufficient seeds were planted to produce several seedlings per inch in each row. The flats were then placed in a greenhouse maintained at 70° to 85° F. (21° to 30° C.) and watered daily by sprinkler.

In the case of pre-emergent testing the herbicide was incorporated into the soil prior to planting of the seeds, at a rate equivalent to the indicated amounts in the Table.

In post-emergent testing chemical application is made by spraying 12 days after planting. The spray solution is prepared by dissolving 60 mg of herbicide compound in 20 ml of acetone containing 1% Tween ®20 (polyoxysorbitan monolaurate), then adding 20 ml of water to the resulting solution. The solution is sprayed at 80 gallon/acre, resulting in a 4 lb/acre rate of chemical application. Other rates were achieved by varying the solution concentration and/or the rate of spray.

In both instances, either pre- or post-emergent testing, approximately 12-14 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in the Tables below.

TABLE I

| | | | HERBICIDE TEST RESULTS | | | | | | | | | | | | | | |
|---|---|---|---|---|---|---|---|---|---|---|---|---|---|---|---|---|---|
| | Application | | | | | | | | Percent Control | | | | | | | | |
| Test | Rate | | Broadleaf weeds | | | | | | | | Grasses | | | | | | |
| Compound | (lb/A) | Method | AMG A | CB B | SES C | VL D | MD E | SP F | PW G | AVE | YNS H | DB I | FT J | ARG K | WG L | SHC M | WO N | AVE |
| 1 | ¼ | PRE | 0 | 0 | 0 | 0 | 0 | 0 | 90 | 12 | 0 | 0 | 0 | 0 | 0 | 0 | 0 | 0 |
| | ½ | | 0 | 0 | 25 | 0 | 35 | 0 | 100 | | 0 | 0 | 0 | 0 | 15 | 0 | 0 | |
| | 1 | | 20 | 0 | 95 | 95 | 100 | 0 | 100 | | 50 | 30 | 85 | 20 | 65 | 60 | 40 | |
| | 2 | | 50 | 0 | 100 | 100 | 100 | 30 | 100 | | 65 | 70 | 98 | 75 | 70 | 90 | 40 | |
| 1 | ¼ | POST | 100 | 100 | 100 | 100 | 100 | 85 | 100 | | 0 | 15 | 90 | 60 | 50 | 50 | 20 | |
| | ½ | | 100 | 100 | 100 | 100 | 100 | 100 | 100 | 100 | 0 | 60 | 100 | 80 | 55 | 70 | 35 | |
| | 1 | | 100 | 100 | 100 | 100 | 100 | 100 | 100 | 100 | 0 | 60 | 100 | 100 | 85 | 90 | 65 | |
| | 2 | | 100 | 100 | 100 | 100 | 100 | 100 | 100 | 100 | 20 | 80 | 100 | 100 | 100 | 100 | 100 | |
| 2 | ¼ | PRE | 0 | 0 | 0 | 0 | 0 | 0 | 20 | 0 | 0 | 0 | 35 | 10 | 0 | 0 | 0 | 8 |
| | ½ | | 0 | 0 | 0 | 30 | 20 | 0 | 40 | 13 | 0 | 0 | 50 | 20 | 0 | 20 | 0 | 15 |
| | 1 | | 20 | 0 | 35 | 55 | 40 | 20 | 80 | 36 | 0 | 20 | 75 | 35 | 30 | 40 | 0 | 33 |
| | 2 | | 35 | 20 | 55 | 75 | 80 | 40 | 100 | 58 | 0 | 35 | 95 | 45 | 55 | 75 | 0 | 51 |
| 2 | ¼ | POST | 65 | 40 | 100 | 100 | 70 | 20 | 80 | 68 | 0 | 0 | 0 | 0 | 0 | 20 | 0 | 3 |
| | ½ | | 100 | 70 | 100 | 100 | 100 | 40 | 90 | 86 | 0 | 10 | 10 | 0 | 0 | 30 | 0 | 8 |
| | 1 | | 100 | 80 | 100 | 100 | 100 | 50 | 95 | 89 | 0 | 20 | 30 | 35 | 20 | 35 | 20 | 27 |

TABLE I-continued

HERBICIDE TEST RESULTS

Percent Control

| Test Compound | Application Rate (lb/A) | Method | Broadleaf weeds | | | | | | | | Grasses | | | | | | | |
|---|---|---|---|---|---|---|---|---|---|---|---|---|---|---|---|---|---|---|
| | | | AMG A | CB B | SES C | VL D | MD E | SP F | PW G | AVE | YNS H | DB I | FT J | ARG K | WG L | SHC M | WO N | AVE |
| | 2 | | 100 | 100 | 100 | 100 | 100 | 60 | 100 | 95 | 0 | 35 | 60 | 55 | 30 | 45 | 35 | 43 |
| 3 | ¼ | PRE | 0 | 0 | 35 | 60 | 45 | 0 | 0 | 20 | 0 | 0 | 10 | 0 | 0 | 0 | 0 | 2 |
| | ½ | | 0 | 0 | 55 | 80 | 70 | 0 | 80 | 36 | 0 | 0 | 35 | 0 | 0 | 0 | 0 | 6 |
| | 1 | | 20 | 0 | 70 | 100 | 75 | 0 | 80 | 64 | 0 | 0 | 65 | 20 | 20 | 25 | 0 | 22 |
| | 2 | | 40 | 0 | 85 | 100 | 85 | 0 | 100 | 44 | 0 | 0 | 100 | 40 | 30 | 30 | 0 | 33 |
| 3 | ¼ | POST | 40 | 20 | 80 | 80 | 30 | — | 20 | 40 | 0 | 0 | 0 | 0 | 0 | 20 | 0 | 3 |
| | ½ | | 50 | 40 | 90 | 90 | 35 | — | 30 | 51 | 0 | 0 | 35 | 0 | 0 | 0 | 0 | 6 |
| | 1 | | 60 | 50 | 95 | 95 | 45 | — | 50 | 62 | 0 | 0 | 20 | 0 | 0 | 40 | 10 | 12 |
| | 2 | | 85 | 75 | 100 | 100 | 50 | — | 70 | 75 | 0 | 0 | 25 | 20 | 0 | 45 | 15 | 18 |
| 4 | ¼ | PRE | 0 | 0 | 0 | 0 | 0 | 0 | 0 | 0 | 0 | 0 | 0 | 0 | 0 | 0 | 0 | 0 |
| | ½ | | 0 | 0 | 0 | 10 | 0 | 0 | 0 | 1 | 0 | 0 | 0 | 0 | 0 | 0 | 0 | 0 |
| | 1 | | 0 | 0 | 0 | 15 | 0 | 0 | 0 | 2 | 0 | 0 | 0 | 0 | 0 | 0 | 0 | 0 |
| | 2 | | 0 | 0 | 0 | 30 | 0 | 0 | 20 | 7 | 0 | 0 | 0 | 0 | 0 | 0 | 0 | 0 |
| 4 | ¼ | POST | | | | | | | | | | | | | | | | |
| | ½ | | | | | | | | | | | | | | | | | |
| | 1 | | | | | | | | | | | | | | | | | |
| | 2 | | 35 | 45 | 60 | 75 | 30 | | 40 | 49 | 20 | 0 | 15 | | 25 | 40 | 0 | |

Compounds
1 O—methyl,2-nitro-5-[2-chloro-4-trifluoromethylphenoxy]benzylmethylphosphinate
2 2-nitro-5-[2-chloro-4-trifluoromethylphenoxy]styryl-3′-O,O—dimethylphosphonate
3 2-nitro-5-[2-chloro-4-trifluoromethylphenoxy]styryl-3′-O,O—di-ethylphosphonate
4 2-nitro-5-[2,4-dichlorophenoxy]-styryl-3′-O,O—diethylphosphonate

TABLE II

HERBICIDE TEST RESULTS

| Compound | Application Rate (lb/A) | Method | Crops | | | | | | |
|---|---|---|---|---|---|---|---|---|---|
| | | | SOY O | RC P | COT Q | CN R | WH S | ML T | SB U |
| 1 | ¼ | PRE | 0 | 0 | 0 | 0 | 0 | 0 | 65 |
| | ½ | | 0 | 0 | 10 | 0 | 0 | 30 | 70 |
| | 1 | | 10 | 25 | 30 | 20 | 40 | 80 | 90 |
| | 2 | | 10 | 45 | 40 | 55 | 65 | 98 | 100 |
| 1 | ¼ | POST | 95 | 35 | 100 | 20 | 75 | 15 | 100 |
| | ½ | | 90 | 35 | 100 | 30 | 70 | 45 | 80 |
| | 1 | | 90 | 50 | 100 | 75 | 70 | 60 | 100 |
| | 2 | | 90 | 60 | 100 | 100 | 60 | 100 | 100 |
| 2 | ¼ | PRE | 0 | 0 | 0 | 0 | 0 | 0 | 20 |
| | ½ | | 0 | 0 | 0 | 0 | 0 | 0 | 40 |
| | 1 | | 20 | 20 | 30 | 0 | 0 | 0 | 45 |
| | 2 | | 35 | 40 | 50 | 0 | 0 | 20 | 70 |
| 2 | ¼ | PRE | 35 | 0 | 100 | 0 | 0 | 10 | 50 |
| | ½ | | 45 | 0 | 100 | 0 | 0 | 20 | 100 |
| | 1 | | 70 | 10 | 100 | 0 | 10 | 25 | 100 |
| | 2 | | 75 | 25 | 100 | 20 | 20 | 40 | 100 |
| 3 | ¼ | PRE | 0 | 0 | 0 | 0 | 0 | 0 | 25 |
| | ½ | | 0 | 0 | 20 | 0 | 0 | 0 | 75 |
| | 1 | | 0 | 0 | 30 | 0 | 0 | 0 | 100 |
| | 2 | | 0 | 0 | 35 | 0 | 20 | 25 | 100 |
| 3 | ¼ | POST | 70 | 20 | 40 | 0 | 0 | 20 | 20 |
| | ½ | | 80 | 30 | 60 | 35 | 0 | 20 | 35 |
| | 1 | | 90 | 35 | 70 | 65 | 0 | 20 | 40 |
| | 2 | | 95 | 50 | 80 | 100 | 10 | 20 | 60 |
| 4 | ¼ | PRE | 0 | 0 | 0 | 0 | 0 | 0 | 0 |
| | ½ | | 0 | 0 | 0 | 0 | 0 | 0 | 0 |
| | 1 | | 0 | 0 | 0 | 0 | 0 | 0 | 0 |
| | 2 | | 0 | 0 | 0 | 0 | 0 | 0 | 0 |
| 4 | ¼ | POST | | | | | | | |
| | ½ | | | | | | | | |
| | 1 | | | | | | | | |
| | 2 | | 35 | 20 | 65 | 25 | 0 | 25 | 45 |

| Compound | Application Rate (lb/A) | Method | Crops | | | | | | | |
|---|---|---|---|---|---|---|---|---|---|---|
| | | | SOY O | AMG P | SP Q | VL R | MO S | GF T | SB U | AVE |
| 5 | ¼ | POST | 40 | 30 | 30 | 70 | 10 | 30 | 30 | 35 |
| | ¼ | | 40 | 40 | 20 | 90 | 30 | 60 | 60 | 45 |
| | ½ | | 50 | 100 | 30 | 90 | 30 | 30 | 60 | 68 |
| | 1 | | 75 | 60 | 50 | 100 | 70 | 40 | 60 | 70 |
| 5 | ¼ | PRE | 10 | 0 | 0 | 0 | 0 | 10 | 20 | 0 |
| | 1 | | 0 | 0 | 90 | 50 | 40 | 70 | 60 | 40 |
| 6 | ¼ | PRE | 10 | 0 | 0 | 50 | 10 | 30 | 60 | 23 |
| | ½ | | 50 | 0 | 10 | 80 | 30 | 30 | 50 | 38 |
| | ¼ | | 70 | 20 | 20 | 90 | 20 | 40 | 40 | 43 |

TABLE II-continued
HERBICIDE TEST RESULTS

| | | | | | | | | | | |
|---|---|---|---|---|---|---|---|---|---|---|
| | 1 | | 40 | 60 | 40 | 90 | 30 | 40 | 40 | 50 |
| 6 | ½ | PRE | 0 | 0 | 0 | 0 | 0 | 30 | 0 | 0 |
| | 1 | | 0 | 0 | 80 | 0 | 0 | 80 | 40 | 20 |

Compounds
1 O—methyl,2-nitro-5-[2-chloro-4-trifluoromethylphenoxy]benzylmethylphosphinate
2 2-nitro-5-[2-chloro-4-trifluoromethylphenoxy]styryl-3'-O,O—dimethylphosphonate
3 2-nitro-5-[2-chloro-4-trifluoromethylphenoxy]styryl-3'-O,O—di-ethylphosphonate
4 2-nitro-5-[2,4-dichlorophenoxy]styryl-3'-O,O—diethylphosphonate
5 O—methyl-2-bromo-5-[2-chloro-4-trifluoromethylphenoxy]benzylmethylphosphonate
6 O—ethyl-2-bromo-5-[2-chloro-4-trifluoromethylphenoxy]benzylmethylphosphonate.

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anti-caking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with macroscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 1530 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. IN GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. A method for controlling undesirable weed pests which comprises applying to the locus were control is desired a herbicidally effective amount of a compound having the formula

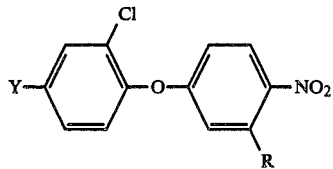

wherein Y is chlorine or trifluoromethyl, and wherein R is selected from those having the formula

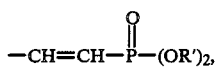

in which R' is selected from the group consisting of lower alkyl groups having from 1 to 3 carbon atoms and agriculturally acceptable salts thereof.

2. The method of claim 1 in which Y is trifluoromethyl, R is

and R' is methyl.

3. As compounds, diphenyl ether derivatives of the formula

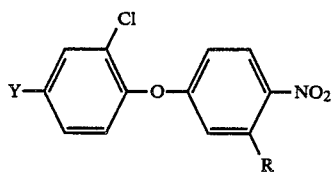

wherein Y is chlorine or trifluoromethyl, and wherein R is selected from those having the formula

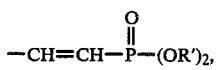

in which R' is selected from the group consisting of lower alkyl groups having from 1 to 3 carbon atoms.

4. The compound of claim 3 in which Y is trifluoromethyl, R is

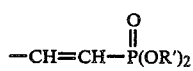

and R' is methyl.

5. The compound of claim 3 in which Y is chlorine, R is

and R' is ethyl.

6. The compound of claim 3 in which Y is trifluoromethyl, R is

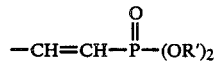

and R' is ethyl.

7. A herbicidal composition which comprises a herbicidally effective amount of a diphenyl ether derivative having the formula

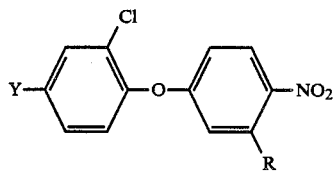

wherein Y is chlorine or trifluoromethyl and wherein R is selected from those having the formula

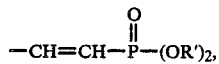

in which R' is selected from the group consisting of lower alkyl groups having from 1 to 3 carbon atoms.

8. The composition of claim 7 in which Y is trifluoromethyl, R is

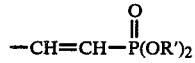

and R' is methyl.

9. The composition of claim 7 in which Y is chlorine, R is

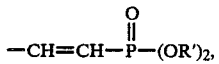

and R' is ethyl.

10. The composition of claim 7 in which Y is trifluoromethyl, R is

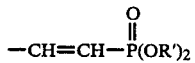

and R' is ethyl.

* * * * *